United States Patent [19]

Roberts et al.

[11] Patent Number: 5,104,994
[45] Date of Patent: Apr. 14, 1992

[54] N-PHENYLPYRAZOLE DERIVATIVES

[75] Inventors: David A. Roberts, London; David W. Hawkins; Ian G. Buntain, both of Essex; Ross McGuire, Ongar Essex, all of England

[73] Assignee: Rhone-Poulenc Agriculture Ltd, Essex, England

[21] Appl. No.: 539,566

[22] Filed: Jun. 18, 1990

[30] Foreign Application Priority Data

Jun. 16, 1989 [GB] United Kingdom ................ 8913866

[51] Int. Cl.$^5$ ........................................... C07D 231/14
[52] U.S. Cl. ................................................. 548/376
[58] Field of Search ......................................... 548/376

[56] References Cited

U.S. PATENT DOCUMENTS 4,918,085  4/1990  D'Silva et al. ...................... 548/376

FOREIGN PATENT DOCUMENTS 213280  3/1989  Japan ................................. 548/376
WO87/03781  7/1987  PCT Int'l Appl. .

Primary Examiner—Mary C. Lee
Assistant Examiner—Joseph K. McKane
Attorney, Agent, or Firm—Burns, Doane, Swecker & Mathis

[57] ABSTRACT

The invention provides N-phenylpyrazole derivatives of the formula:

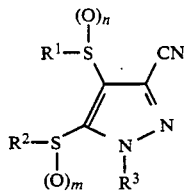

wherein $R^1$ represents alkyl optionally substituted by halogen, $R^2$ represents an optionally substituted aryl or aralkyl group, $R^3$ represents a phenyl group substituted in the 2-position by halogen; in the 4-position by optionally halo substituted alkyl or alkoxy; and optionally in the 6-position by halogen; and m and n are independently 0, 1 or 2; which are active against arthropod, plant nematode, helminth and protozoal pests.

7 Claims, No Drawings

N-PHENYLPYRAZOLE DERIVATIVES

This invention relates to N-phenylpyrazole derivatives, to compositions containing them and to the use of N-phenylpyrazole derivatives against arthropod, plant nematode, helminth and protozoan pests.

Japanese Specification No. 213280, published on 3rd March 1989 describes pyrazole derivatives of the formula:

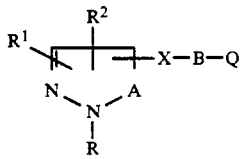

wherein

A represents —CO— or

provided that a double bond is formed between the 4 and 5-positions of the pyrazole ring;

X represents O or S;

Q represents optionally substituted phenyl or optionally substituted heterocyclyl;

B represents:

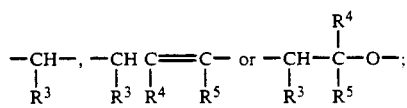

wherein $R^3$, $R^4$ and $R^5$ represent hydrogen or alkyl of 1 to 4 carbon atoms;

$R^1$ and $R^2$ represent hydrogen, halogen (but not both halogen), cyano, nitro, OH, —C=N($R^6$)—$OR^7$; optionally substituted alkyl of 1 to 4 carbon atoms, optionally substituted alkoxy of 1 to 4 carbon atoms, optionally substituted alkylthio of 1 to 4 carbon atoms, optionally substituted phenylthio, optionally substituted phenyl, optionally substituted heterocyclyl or —$COOR^8$;

$R^6$ and $R^7$ represent hydrogen or optionally substituted alkyl of 1 to 4 carbon atoms;

$R^8$ represents alkenyl of 2 to 8 carbon atoms, alkynyl of 2 to 8 carbon atoms or optionally substituted alkyl of 1 to 4 carbon atoms;

R represents optionally substituted alkyl of 1 to 16 carbon atoms, optionally substituted alkenyl of 2 to 16 carbon atoms, optionally substituted alkynyl of 2 to 16 carbon atoms, optionally substituted cycloalkyl of 3 to 8 carbon atoms, oxacycloalkyl of 5 to 8 carbon atoms, optionally substituted thiocycloalkyl of 5 to 8 carbon atoms, optionally substituted phenyl or optionally substituted heterocyclyl. The pyrazole derivatives are stated to be useful as insecticides and acaricides. 1,000 ppm of the compounds of formula (I) are reported to be 100% insecticidally effective against larvae of Epilachna vigitioctomaculata and 100% acaricidally effective against larvae of Tegranychus kanzawai.

It has been discovered that a group of compounds part of which falls within the general formula depicted above possess unexpectedly advantageous properties. The new compounds possess activity against arthropod, plant nematode, helminth and protozoan pests. In tests for activity described hereinafter compounds of the invention tested produce 100% and 88% mortality, respectively, at 20 ppm against larvae of Spodoptera littoralis and 100% mortality at 0.5 or 1 ppm against larvae of Diabrotica undecimpunctata. The new compounds are depicted in formula (I) hereinafter; no compound falling within general formula (I) is described in the published Japanese specification.

The present invention provides N-phenylpyrazole derivatives of the general formula (I) depicted herein after wherein:

$R^1$ represents a straight or branched chain alkyl group containing up to 4 carbon atoms which may be unsubstituted or substituted by one or more halogen atoms;

$R^2$ represents an optionally substituted aryl (e.g. phenyl) or aralkyl (e.g. benzyl) group;

$R^3$ represents a phenyl group substituted in the 2-position by a halogen atom; in the 4-position by a straight or branched chain alkyl or alkoxy group containing from 1 to 4 carbon atoms which may be unsubstituted or substituted by one or more halogen atoms; and optionally in the 6-position by a halogen atom; and m and n are independently 0, 1 or 2; which have valuable activity against arthropod, plant nematode, helminth and protozoan pests, more particularly by ingestion of the compound(s) of general formula (I) by the arthropods.

The group $R^2$ may be optionally substituted on the aromatic ring by one or more halogen atoms; optionally halogenated alkyl, alkoxy, alkylthio, alkylsulphinyl or alkylsulphonyl groups each containing up to 4 carbon atoms and being straight or branched chain; or nitro, cyano or acyl groups. In addition, when $R^2$ represents an aralkyl group, it may also be α-substituted by a straight or branched chain alkyl group containing up to 4 carbon atoms.

Compounds of general formula (I), processes for their preparation, compositions containing them and methods for their use constitute features of the present invention.

It is to be understood that the halogen atoms are fluorine, chlorine, bromine or iodine; the halogen atoms on the phenyl group $R^3$ may be the same or different and that when the groups $R^1$ and $R^2$ are substituted by more than one halogen atom these atoms may also be the same or different.

Preferred compounds of general formula (I) are those wherein $R^1$ represents a trihalomethyl and more preferably a trifluoromethyl group.

Compounds of general formula (I) wherein the 4-position in the phenyl group represented by $R^3$ is substituted by the trifluoromethyl or trifluoromethoxy group are preferred.

Preferred compounds of general formula (I) are those with phenyl ($R^3$) substitution which is 2,6-dichloro-4-difluoromethoxy, 2-chloro-4-trifluoromethyl, 2-bromo-6-chloro- 4-trifluoromethyl, 2,6-dibromo-4-trifluoromethyl or 2-bromo-4-trifluoromethyl.

Compounds of general formula I) with 2,6-dichloro-4-trifluoromethyl or 2,6-dichloro-4-trifluoromethoxy substitution of the phenyl group ($R^3$) are especially preferred.

Compounds of general formula (I) which are of particular interest are:

1. 3-Cyano-1-(2,6-dichloro-4-trifluoromethylphenyl)-5-phenylthio-4-trifluoromethylthiopyrazole
2. 5-Benzylthio-3-cyano-1-(2,6-dichloro-4-trifluoromethylphenyl)-4-trifluoromethylsulphonylpyrazole The numbers 1 and 2 are assigned to the above compounds for identification and reference hereinafter.

According to a feature of the present invention, there is provided a method for the control of arthropod, plant nematode, helminth or protozoan pests at a locus which comprises the treatment of the locus (e.g. by application or administration) with an effective amount of a compound of general formula (I), wherein the various symbols are as hereinbefore defined. The compounds of general formula (I may, in particular, be used in the field of veterinary medicine and livestock husbandry and in the maintenance of public health against arthropods, helminths or protozoa which are parasitic internally or externally upon vertebrates, particularly warm-blooded vertebrates, for example man and domestic animals, e.g. cattle, sheep, goats, equines, swine, poultry, dogs, cats and fishes,. for example Acarina, including ticks (e.g. Ixodes spp., Boophilus spp. e.g. *Boophilus microplus,* Amblyomma spp., Hyalomma spp., Rhipicephalus spp. e.g. *Rhipicephalus appendiculatus,* Haemaphysalis spp., Dermacentor spp., Ornithodorus spp. (e.g. *Ornithodorus moubata* and mites (e.g. Damalinia spp., *Dermahyssus gallinae,* Sarcoptes spp. e.g. *Sarcoptes scabiei,* Psoroptes spp., Chorioptes spp., Demodex spp., Eutrombicula spp.,; Diptera (e.g. Aedes spp., Anopheles spp., Musca spp., Hypoderma spp., Gasterophilus spp., Simulium spp.); Hemiptera (e.g. . Triatoma spp.); Phthiraptera (e.g. Damalinia spp., Linognathus spp. ; Siphonaptera (e.g. Ctenocephalides spp.); Dictyoptera (e.g. Periplaneta spp., Blatella spp. ; Hymenoptera (e.g. *Monomorium pharaonis*); for example against infections of the gastro-intestinal tract caused by parasitic nematode worms, for example embers of the family Trichostrongylidae, *Nippostrongylus brasiliensis, Trichinella spiralis, Haemonchus contortus, Trichostrongylus colubriformis, Nematodirus battus, Ostertagia circumcincta, Trichostrongylus axei,* Cooperia spp. and *Hymenolepis nana;* in the control and treatment of protozoal diseases caused by, for example, Eimeria spp. e.g. *Eimeria tenella, Eimeria acervulina, Eimeria brunetti, Eimeria maxima* and *Eimeria necatrix, Trypanosoma cruzi,* Leishmania spp., Plasmodium spp., Babesia spp., Trichomonadidae spp., Histomonas spp., Giardia spp., Toxoplasma spp., *Entamoeba histolytica* and Theileria spp.; in the protection of stored products, for example cereals, including grain and flour, groundnuts, animal feedstuffs, timber and household goods, e.g. carpets and textiles, against attack by arthropods, more especially beetles, including weevils, moths and mites, for example Ephestia spp. (flour moths), Anthrenus spp. (carpet beetles), Tribolium spp. (flour beetles), Sitophilus spp. grain weevils) and Acarus spp. (mites , in the control of cockroaches, ants and termites and similar arthropod pests in infested domestic and industrial premises and in the control of mosquito larvae in waterways, wells, reservoirs or other running or standing water; for the treatment of foundations, structure and soil in the prevention of the attack on buildings by termites, for example, Reticulitermes spp., Heterotermes spp., Coptotermes spp.; in agriculture, against adults, larvae and eggs of Lepidoptera (butterflies and moths), e.g. Heliothis spp. such as *Heliothis virescens* (tobacco budworm), *Heliothis armigera* and *Heliothis zea,* Spodoptera spp. such as *S.exempta, S.littoralis* (Egyptian cotton worm), *S.eridania* (southern army worm), *Mamestra configurata* bertha army worm); Earias spp. e.g. E.insulana (Egyptian bollworm), Pectinophora spp. e.g. *Pectinophora gossypiella* (pink bollworm), Ostrinia spp. such as *O.nubilalis* (European cornborer), *Trichoplusia ni* (cabbage looper), Pieris spp. (cabbage worms), Laphygma spp. (army worms), Agrotis and Amathes spp. (cutworms , Wiseana spp. (porina moth), Chilo spp. (rice stem borer , Tryporyza spp. and Diatraea spp. (sugar cane borers and rice borers , *Sparganothis pilleriana* (grape berry moth), *Cydia pomonella* (codling moth), Archips spp. (fruit tree tortrix moths), *Plutella xylostella* (diamond back moth); against adult and larvae of Coleoptera (beetles) e.g. *Hypothenemus hampei* (coffee berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms , Agriotes spp. (wireworms), Dermolepida and Heteronychus spp. (white grubs), *Phaedon cochleariae* (mustard beetle), *Lissorhoptrus oryzophilus* (rice water weevil), Meligethes spp. (pollen beetles , Ceutorhynchus spp., Rhynchophorus and Cosmopolites spp. (root weevils); against Hemiptera e.g. Psylla spp., Bemisia spp., Trialeurodes spp., Aphis spp., Myzus spp., *Megoura viciae,* Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseucoccus spp., Helopeltis spp. (mosquito bugs), Lygus spp., Dysdercus spp., Oxycarenus spp., Nezara spp.; Hymenoptera e.g. Athalia spp. and Cephus spp. (saw flies), Atta spp. leaf cutting ants); Diptera e.g. Hylemyia spp. (root flies), Atherigona spp. and Chlorops spp. (shoot flies), Phytomyza spp. (leaf miners), Ceratitis spp. (fruit flies); Thysanoptera such as *Thrips tabaci;* Orthoptera such as Locusta and Schistocerca spp. (locusts) and crickets e.g. Gryllus spp. and Acheta spp.; Collembola e.g. Sminthurus spp. and Onychiurus spp. (springtails), Isoptera e.g. Odontotermes spp. (termites), Dermaptera e g. Forficula spp. (earwigs) and also other arthropods of agricultural significance such as Acari (mites) e.g. Tetranychus spp., Panonychus spp. and Bryobia spp. (spider mites), Eriophyes spp. (gall mites), Polyphagotarsonemus spp.; Blaniulus spp. (millipedes), Scuticerella spp. (symphilids), Oniscus spp. (woodlice) and Triops spp. (crustacea); nematodes which attack plants and trees of importance to agriculture, forestry and horticulture either directly or by spreading bacterial, viral, mycoplasma or fungal diseases of the plants, root-knot nematodes such as Meloidogyne spp. (e.g. *M. incognita*); cyst nematodes such as Globodera spp. e.g. *G. rostochiensis*); Heterodera spp. e.g. *H. avenae*); Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

The invention also provides a method for the control of arthropod or nematode pests of plants which comprises the application to the plants or to the medium in which they grow of an effective amount of a compound of general formula (I).

For the control of arthropods and nematodes, the active compound is generally applied to the locus in which arthropod or nematode infestation is to be controlled at a rate of about 0.1 kg to about 25 kg of active compound per hectare of locus treated. Under ideal conditions, depending on the pest to be controlled, the lower rate may offer adequate protection. On the other hand, adverse weather conditions, resistance of the pest and other factors ay require that the active ingredient be used in higher proportions. In foliar application, a rate of 1 g to 1000 g/ha may be used.

When the pest is soil-borne, the formulation containing the active compound is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The compounds of general formula (I) may be applied in solid or liquid compositions to the soil principally to control those nematodes dwelling therein but also to the foliage principally to control those nematodes attacking the aerial parts of the plants (e.g. Aphelenchoides spp. and Ditylenchus spp. listed above).

The compounds of general formula (I) are of value in controlling pests which feed on parts of the plant remote from the point of application, e.g. leaf feeding insects are killed by the subject compounds applied to roots.

In addition the compounds may reduce attacks on the plant by means of antifeeding or repellent effects.

The compounds of general formula (I) are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids), or termites, for example, Reticulitermes spp., Heterotermes spp., Coptotermes spp.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form e.g. as carpets or textiles) from moth and beetle attack; also stored meat and fish from beetle, mite and fly attack.

The compounds of general formula (I) are of particular value in the control of arthropods, helminths or protozoa which are injurious to, or spread or act as vectors of diseases in man and domestic animals, for example those hereinbefore mentioned, and ore especially in the control of ticks, mites, lice, fleas, midges and biting, nuisance and myiasis flies. The compounds of general formula (I) are particularly useful in controlling arthropods, helminths or protozoa which are present inside domestic host animals or which feed in or on the skin or suck the blood of the animal, for which purpose they may be administered orally, parenterally, percutaneously or topically.

Coccidiosis, a disease caused by infections by protozoan parasites of the genus Eimeria, is an important potential cause of economic loss in domestic animals and birds, particularly those raised or kept under intensive conditions. For example, cattle, sheep, pigs and rabbits may be affected, but the disease is especially important in poultry, in particular chickens.

The poultry disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have had their market value substantially reduced as a result of the infection.

Administration of a small amount of a compound of general formula (I preferably by combination with poultry feed is effective in preventing or greatly reducing the incidence of coccidiosis. The compounds are effective against both the cecal form (caused by *E. tenella*) and the intestinal forms (principally caused by *E. acervulina, E. brunetti, E. maxima* and *E. necatrix*).

The compounds of general formula (I) also exert an inhibitory effect on the oocysts by greatly reducing the number and or the sporulation of those produced.

The compositions hereinafter described for topical application to man and animals and in the protection of stored products, household goods, property and areas of the general environment may, in general, alternatively be employed for application to growing crops and crop growing loci and as a seed dressing.

Suitable means of applying the compounds of general formula (I) include:

to persons or animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax-smears and livestock self-treatment systems; to the environment in general or to specific locations where pests may lurk, including stored products, timber, household goods, and domestic and industrial premises, as sprays, fogs, dusts, smokes, wax-smears, lacquers, granules and baits, and in tricklefeeds to waterways, wells, reservoirs and other running or standing water; to domestic animals in feed to control fly larvae feeding in their faeces;

to growing crops as foliar sprays, dusts, granules, fogs and foams; also as suspensions of finely divided and encapsulated compounds of general formula I ; as soil and root treatments by liquid drenches, dusts, granules, smokes and foams; and as seed dressings by liquid slurries and dusts.

The compounds of general formula (I) may be applied to control arthropods, helminths or protozoa in compositions of any type known to the art suitable for internal or external administration to vertebrates or application for the control of arthropods in any premises or indoor or outdoor area, containing as active ingredient at least one compound of general formula (I) in association with one or more compatible diluents or adjuvants appropriate for the intended use. All such compositions may be prepared in any manner known to the art.

Compositions suitable for administration to vertebrates or man include preparations suitable for oral, parenteral, percutaneous, e.g. pour-on, or topical administration.

Compositions for oral administration comprise one or more of the compounds of general formula (I) in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or pour-on preparations and devices (e.g. ear tags) attached externally to animals in such a way as to provide local or systemic arthropod control.

Solid or liquid baits suitable for controlling arthropods comprise one or more compounds of general formula (I) and a carrier or diluent which may include a food substance or some other substance to induce consumption by the arthropod.

Liquid compositions include water miscible concentrates, emulsifiable concentrates, flowable suspensions, wettable or soluble powders containing one or more compounds of general formula (I) which may be used to treat substrates or sites infested or liable to infestation by arthropods including premises, outdoor or indoor storage or processing areas, containers or equipment and standing or running water.

Solid homogenous or heterogenous compositions containing one or more compounds of general formula (I), for example granules, pellets, briquettes or capsules, may be used to treat standing or running water over a period of time. A similar effect may be achieved using trickle or intermittent feeds of water dispersible concentrates as described herein.

Compositions in the form of aerosols and aqueous or non-aqueous solutions or dispersions suitable for spraying, fogging and low- or ultra-low volume spraying may also be used.

Suitable solid diluents which may be used in the preparation of compositions suitable for applying the compounds of general formula (I) include aluminium silicate, kieselguhr, corn husks, tricalcium phosphate, powdered cork, absorbent carbon black, magnesium silicate, a clay such as kaolin, bentonite or attapulgite, and water soluble polymers and such solid compositions may, if desired, contain one or more compatible wetting, dispersing, emulsifying or colouring agents which, when solid, may also serve as diluent.

Such solid compositions, which may take the form of dusts, granules or wettable powders, are generally prepared by impregnating the solid diluents with solutions of the compound of general formula (I) in volatile solvents, evaporating the solvents and, if necessary, grinding the products so as to obtain powders and, if desired, granulating or compacting the products so as to obtain granules, pellets or briquettes or by encapsulating finely divided active ingredient in natural or synthetic polymers, e.g. gelatin, synthetic resins and polyamides.

The wetting, dispersing and emulsifying agents which may be present, particularly in wettable powders, may be of the ionic or non-ionic types, for example sulphoricinoleates, quaternary ammonium derivatives or products based upon condensates of ethylene oxide with nonyl- and octyl-phenol, or carboxylic acid esters of anhydrosorbitols which have been rendered soluble by etherification of the free hydroxy groups by condensation with ethylene oxide, or mixtures of these types of agents. Wettable powders may be treated with water immediately before use to give suspensions ready for application.

Liquid compositions for the application of the compounds of general formula (I may take the form of solutions, suspensions and emulsions of the compounds of general formula (I) optionally encapsulated in natural or synthetic polymers, and may, if desired, incorporate wetting, dispersing or emulsifying agents. These emulsions, suspensions and solutions may be prepared using aqueous, organic or aqueous-organic diluents, for example acetophenone, isophorone, toluene, xylene, mineral, animal or vegetable oils, and water soluble polymers (and mixtures of these diluents), which may contain wetting, dispersing or emulsifying agents of the ionic or non-ionic types or mixtures thereof, for example those of the types described above. When desired, the emulsions containing the compounds of general formula (I) may be used in the form of self-emulsifying concentrates containing the active substance dissolved in the emulsifying agents or in solvents containing emulsifying agents compatible with the active substance, the simple addition of water to such concentrates producing compositions ready for use.

Compositions containing compounds of general formula (I) which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as apropriate e.g. benomyl, iprodione), bactericides, arthropod or vertebrate attractants or repellents or pheromones, reodorants, flavouring agents, dyes and auxiliary therapeutic agents, e.g trace elements. These may be designed to improve potency, persistence, safety, uptake where desired, spectrum of pests controlled or to enable the composition to perform other useful functions n the same animal or area treated.

Examples of other pesticidally-active compounds which may be included in, or used in conjunction with, the compositions of the present invention are: acephate, chlorpyrifos, demeton-S-methyl, disulfoton, ethoprofos, fenitrothion, malathion, monocrotophos, parathion, phosalone, pirimiphos-methyl, triazophos, cyfluthrin, cypermethrin, deltamethrin, fenpropathrin, fenvalerate, permethrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectin, milbemycins, thiophanate, trichlorfon, dichlorvos, diaveridine and dimetridazole.

The compositions for application to control arthropod, plant nematode, helminth or protozoan pests usually contain from 0.00001% to 95%, more particularly from 0.0005% to 50%, by weight of one or more compounds of general formula (I) or of total active ingredients (that is to say the compound(s) of general formula (I) together with other substances toxic to arthropods and plant nematodes, anthelmintics, anticoccidials, synergists, trace elements or stabilisers). The actual compositions employed and their rate of application will be selected to achieve the desired effect(s) by the farmer, livestock producer, medical or veterinary practitioner, pest control operator or other person skilled in the art. Solid and liquid compositions for application topically to animals, timber, stored products or household goods usually contain from 0.00005% to 90%, ore particularly from 0.001% to 10%, by weight of one or more compounds of general formula (I). For administration to animals orally or parenterally, including percutaneously solid and liquid compositions normally contain from 0.1% to 90% by weight of one or more compound of general formula (I). Medicated feedstuffs normally contain from 0.001% to 3% by weight of one or more compounds of general formula (I). Concentrates and supplements for mixing with feedstuffs normally contain from 5% to 90%, and preferably from 5% to 50%, by weight of one or more compounds of general formula (I). Mineral salt licks normally contain from 0.1% to 10% by weight of one or more compounds of general formula (I).

Dusts and liquid compositions for application to livestock, persons, goods, premises or outdoor areas may contain 0.0001% to 15%, and more especially 0.005% to 2.0%, by weight of one or more compounds of general formula (I). Suitable concentrations in treated waters are between 0.0001 ppm and 20 ppm, and more especially 0.001 ppm to 5.0 ppm. of one or more compounds of general formula (I) and may also be used therapeutically in fish farming with appropriate exposure times. Edible baits may contain from 0.01% to 5% and preferably 0.01% to 1.0%, by weight of one or more compounds of general formula (I).

When administered to vertebrates parenterally, orally or by percutaneous or other means, the dosage of compounds of general formula (I) will depend upon the species, age and health of the vertebrate and upon the nature and degree of its actual or potential infestation by arthropod, helminth or protozoan pest. A single dose of 0.1 to 100 mg, preferably 2.0 to 20.0 mg, per kg body weight of the animal or doses of 0.01 to 20.0 mg, preferably 0.1 to 5.0 mg, per kg body weight of the animal per day for sustained medication are generally suitable by oral or parenteral administration. By use of sustained release formulations or devices, the daily doses required over a period of months may be combined and administered to animals on a single occasion.

In experiments on activity against arthropods carried out on representative compounds, the following results (wherein ppm indicates the concentration of the compound in parts per million of the test solution applied) have been obtained:

Test species: *Spodoptera littoralis*

French bean leaf discs were set in agar in petri-dishes and infected with 5 larvae (2nd instar). Four replicate dishes were assigned to each treatment and were sprayed under a Potter Tower with the appropriate test dilution. After 2 days live larvae ere transferred to similar dishes containing untreated leaves set in agar. Two or three days later the dishes were removed from the constant temperature (25° C.) room in which they had been held and the mean percentage mortalities of larvae were determined. These data were corrected against the mortalities in dishes treated with 50% aqueous acetone alone which served as controls.

According to the above method, applications of compounds 1 and 2 were effective against the larvae of *Spodoptera littoralis* producing 100% and 88% mortality, respectively, at 20 ppm.

Test species: *Diabrotica undecimpunctata*

Test solutions at appropriate concentrations were applied to loam and thoroughly mixed. The treated soil was then transferred to small pots and infected with five larvae (seven day old) per pot. Four replicate pots were used per test concentration. After seven days at 26° C., the number of dead and live larvae were counted and percentage mortalities determined. These data were corrected against the mortalities observed in pots treated with acetone alone, which served as controls.

According to the above method, an application of compound 1 or 2 was effective against larvae of *Diabrotica undecimounctata*, producing 100% mortality at 1 ppm and 0.5 ppm, respectively (ovendry weight of loam).

The following Composition Examples illustrate compositions for use against arthropod, plant nematode, helminth or protozoan pests which comprise, as active ingredient, compounds of general formula (I). The compositions described in Composition Examples 1 to 6 can each be diluted in water to give a sprayable composition at concentrations suitable for use in the field.

COMPOSITION EXAMPLE 1

A water soluble concentrate was prepared from

| | |
|---|---|
| 3-Cyano-1-(2,6-dichloro-4-trifluoromethyl-phenyl)-5-phenylthio-4-trifluoromethyl-thiopyrazole | 7% w/v |
| Ethylan BCP | 10% w/v |

-continued

| | |
|---|---|
| and N-methylpyrrolidone | to 100% by volume | by dissolving the Ethylan BCP in a portion of N-methylpyrrolidone, and then adding the active ingredient with heating and stirring until dissolved. The resulting solution was made up to volume by adding the remainder of the solvent.

COMPOSITION EXAMPLE 2

An emulsifiable concentrate was prepared from

| | |
|---|---|
| 3-Cyano-1-(2,6-dichloro-4-trifluoromethyl-phenyl)-5-phenylthio-4-trifluoromethyl-thiopyrazole | 7% w/v |
| Soprophor BSU | 4% w/v |
| Arylan CA | 4% w/v |
| N-methylpyrrolidone | 50% w/v |
| and Solvesso 150 | to 100% by volume | by dissolving Soprophor BSU, Arylan CA and the active ingredient in N-methylpyrrolidone, and then adding Solvesso 150 to volume.

COMPOSITION EXAMPLE 3

A wettable powder was prepared from

| | |
|---|---|
| 3-Cyano-1-(2,6-dichloro-4-trifluoromethyl-phenyl)-5-phenylthio-4-trifluoromethyl-thiopyrazole | 40% w/w |
| Arylan S | 2% w/w |
| Darvan No. 2 | 5% w/w |
| and Celite PF | to 100% by weight | by mixing the ingredients, and grinding the mixture in a hammer-mill to a particle size less than 50 microns.

COMPOSITION EXAMPLE 4

An aqueous flowable formulation was prepared from

| | |
|---|---|
| 3-Cyano-1-(2,6-dichloro-4-trifluoromethyl-phenyl)-5-phenylthio-4-trifluoromethyl-thiopyrazole | 30% w/v |
| Ethylan BCP | 1% w/v |
| Sopropon T36 | 0.2% w/v |
| Ethylene glycol | 5% w/v |
| Rhodigel 23 | 0.15% w/v |
| and Water | to 100% by volume | by intimately mixing the ingredients and grinding in a bead mill until the median particle size was less than 3 microns.

COMPOSITION EXAMPLE 5

An emulsifiable suspension concentrate was prepared from

| | |
|---|---|
| 3-Cyano-1-(2,6-dichloro-4-trifluoromethylphenyl)-5-phenylthio-4-trifluoromethylthiopyrazole | 30% w/v |
| Ethylan BCP | 10% w/v |
| Bentone 38 | 0.5% w/v |
| and Solvesso 150 | to 100% by volume | by intimately mixing the ingredients and grinding in a bead mill until the median particle size was less than 3 microns.

COMPOSITION EXAMPLE 6

Water dispersible granules were prepared from

| | |
|---|---|
| 3-Cyano-1-(2,6-dichloro-4-trifluoromethyl-phenyl)-5-phenylthio-4-trifluoromethyl-thiopyrazole | 30% w/w |
| Darvan No. 2 | 15% w/w |
| Arylan S | 8% w/w |
| and Celite PF | to 100% by weight | by mixing the ingredients, micronising in a fluid-energy mill, and then granulating in a rotating pelletiser by spraying on sufficient water (up to 10% w/w). The resulting granules were dried in a fluid-bed drier to remove excess water.

Descriptions of commercial ingredients used in the foregoing Composition Examples:

| | |
|---|---|
| Ethylan BCP | nonylphenol ethylene oxide condensate |
| Soprophor BSU | condensate of tristyrylphenol and ethylene oxide |
| Arylan CA | 70% w/v solution of calcium dodecylbenzenesulphonate |
| Solvesso 150 | light $C_{10}$-aromatic solvent |
| Arylan S | sodium dodecylbenzenesulphonate |
| Darvan | sodium lignosulphonate |
| Celite PF | synthetic magnesium silicate carrier |
| Sopropon T36 | sodium salt of polycarboxylic acid |
| Rhodigel 23 | polysaccharide xanthan gum |
| Bentone 38 | organic derivative of magnesium montmorillonite |

COMPOSITION EXAMPLE 7

A dusting powder may be prepared by intimately mixing:

| | |
|---|---|
| 3-Cyano-1-(2,6-dichloro-4-trifluoromethylphenyl)-5-phenylthio-4-trifluoromethylthiopyrazole | 1 to 10% w/w (weight/weight) |
| Talc superfine | to 100% by weight |

This powder may be applied to a locus of arthropod infestation, for example refuse tips or dumps, stored products or household goods or animals infested by, or at risk of infestation by, arthropods to control the arthropods by oral ingestion. Suitable means for distributing the dusting powder to the locus of arthropod infestation include mechanical blowers, handshakers and livestock self treatment devices.

COMPOSITION EXAMPLE 8

An edible bait may be prepared by intimately mixing:

| | |
|---|---|
| 3-Cyano-1-(2,6-dichloro-4-trifluoromethyl-phenyl)-5-phenylthio-4-trifluoromethyl-thiopyrazole | 0.1 to 1.0% w/w |
| Wheat flour | 80% w/w |
| Molasses | to 100% w/w |

This edible bait may be distributed at a locus, for example domestic and industrial premises, e.g. kitchens, hospitals or stores, or outdoor areas, infested by arthropods, for example ants, locusts, cockroaches and flies, to control the arthropods by oral ingestion.

COMPOSITION EXAMPLE 9

A solution may be prepared containing:

| | |
|---|---|
| 3-Cyano-1-(2,6-dichloro-4-trifluoromethylphenyl)-5-phenylthio-4-trifluoromethylthiopyrazole | 15% w/v (weight/volume) |
| Dimethylsulphoxide | to 100% by volume | by dissolving the pyrazole derivative in a portion of the dimethylsulphoxide and then adding more dimethylsulphoxide to the desired volume. This solution may be applied to domestic animals infested by arthropods, percutaneously as a pour-on application or, after sterilisation by filtration through a polytetrafluoroethylene membrane (0.22 micrometer pore size), by parenteral injection, at a rate of application of from 1.2 to 12 ml of solution per 100 kg of animal body weight.

COMPOSITION EXAMPLE 10

A wettable powder may be formed from:

| | |
|---|---|
| 3-Cyano-1-(2,6-dichloro-4-trifluoromethylphenyl)-5-phenylthio-4-trifluoromethylthiopyrazole | 50% w/w |
| Ethylan BCP a nonylphenol/ethylene oxide condensate containing 9 moles of ethylene oxide per mol of phenol) | 5% w/w |
| Aerosil (silicon dioxide of microfine-particle size) | 5% w/w |
| Celite PF (synthetic magnesium silicate carrier) | 40% w/w | by adsorbing the Ethylan BCP onto the Aerosil, mixing with the other ingredients and grinding the mixture in a hammer-mill to give a wettable powder, which may be diluted with water to a concentration of from 0.001% to 2% w/v of the pyrazole compound and applied to a locus of infestation by arthropods, for example dipterous larvae, or plant nematodes by spraying, or to domestic animals infested by, or at risk of infestation by, arthropods, helminths or protozoa, by spraying or dipping, or by oral administration as drinking water, to control the arthropods, helminths or protozoa.

COMPOSITION EXAMPLE 11

A slow release bolus may be formed from granules containing a density agent, binder, slow-release agent and 3-cyano-1-(2,6-dichloro-4-trifluoromethylphenyl)-5-phenylthio-4-trifluoromethylthiopyrazole compound at varying percentage compositions. By compressing the mixture a bolus with a specific gravity of 2 or more can be formed and may be administered orally to ruminant domestic animals for retention within the reticulo-rumen to give a continual slow release of pyrazole compound over an extended period of time to control infestation of the ruminant domestic animals by arthropods, helminths or protozoa.

COMPOSITION EXAMPLE 12

A slow release composition may be prepared from:

| | |
|---|---|
| 3-Cyano-1-(2,6-dichloro-4-trifluoromethylphenyl)-5-phenylthio-4-trifluoromethylthiopyrazole | 0.5 to 25% w/w |
| polyvinylchloride base | to 100% w/w | by blending the polyvinylchloride base with the pyrazole compound and a suitable plasticiser, e.g. dioctyl phthalate, and melt-extruding or hot-moulding the homogenous composition into suitable shapes, e.g. granules, pellets, brickettes or strips, suitable, for example, for addition to standing water or, in the case of strips, fabrication into collars or ear-tags for attachment to domestic animals, to control insect pests by slow release of the pyrazole compound.

Similar compositions may be prepared by replacing the 3-cyano-1-(2,6-dichloro-4-trifluoromethylphenyl)-5-phenylthio-4-trifluoromethylthiopyrazole in the Composition Examples by the appropriate quantity of any other compound of general formula (I).

The compounds of general formula (I) can be prepared by the application or adaptation of known methods (ie. methods heretofore used or described in the chemical literature), generally pyrazole ring formation followed where necessary by changing substituents.

In the following description when symbols appearing in formulae are not specifically defined it is to be understood that they are "as hereinbefore defined" in accordance with the first definition of each symbol in this specification. According to a feature of the invention there is provided a process for the preparation of a compound of general formula (I) which comprises:

(i) when m=0: reacting a compound of formula (II) wherein Hal represents chlorine, bromine or iodine:

(a) when Hal=bromo or iodo, with an organolithium reagent, e.g. n-butyl lithium, in an inert solvent, e.g. tetrahydrofuran, at a temperature of from $-30°$ to $-90°$ C. and subsequent reaction with a compound of formula:

$$R^2-S-X$$

wherein X is halogen, preferably chlorine, or the cyano group; or with

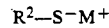

$$R^2-S-S-R^2, \text{ or}$$

(b) when Hal=chloro or bromo, by reaction with a compound of formula:

$$R^2-S^-M^+$$

wherein M is an alkali metal, preferably sodium or potassium, in an inert solvent, e.g. N,N-dimethylformamide, at a temperature from ambient to 100° C.; or (ii) by diazotisation of a compound of formula (III) in the presence of a compound of formula:

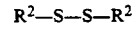

$$R^2-S-S-R^2$$

the diazotisation preferably being achieved using an alkyl nitrite, e.g. t-butyl nitrite, in an inert solvent, e.g. chloroform or acetonitrile, and at a temperature from ambient to reflux (J.Het.Chem. 25, 955, 1988); or (iii) when m=2, reacting a compound of formula (II):

(a) when Hal=bromo or iodo, with an organolithium reagent, e.g. n-butyl lithium, in an inert solvent, e.g. tetrahydrofuran, at a temperature of from $-30°$ to $-90°$ C. and subsequent reaction with a compound of formula:

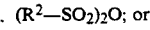

$$(R^2-SO_2)_2O; \text{ or}$$

(b) when Hal=chloro, bromo or iodo, by reaction with a compound of formula:

$$R^2-SO^-{}_2M^+$$

in an inert solvent, e.g.

N-dimethylformamide, at a temperature from ambient to 100° C.; optionally followed by the oxidation of a compound of general formula (I), wherein m and/or n is (a) 0 or (b) 1 into a compound wherein m and/or n is (a) 1 or 2 or (b) 2 generally using either:

(i) reagents of general formula:

R—OOH wherein R is hydrogen, trifluoroacetyl or, preferably 3-chlorobenzoyl, in a solvent, e.g. dichloromethane, chloroform or trifluoroacetic acid, at a temperature from 0° to 60° C.; or (ii) a peroxy salt, such as potassium hydrogen persulphate or the potassium salt of Caro's acid, in a solvent, e.g. methanol and water, at a temperature from −30° to 50° C.

Compounds of formulae (II) and (III) may be obtained according to the methods given in European Patent Application No. 295117.

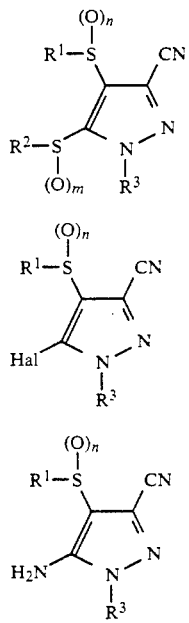

The following Examples and Reference Examples illustrate the preparation of compounds of general formula (I) according to the present invention: [Chromatography was effected on a silica column (May & Baker Ltd 40/60 flash silica) at a pressure of 6.8 Nm$^{-2}$.]

EXAMPLE 1

A solution of 5-amino-3-cyano-1-(2,6-dichloro-4-trifluoromethylphenyl)-4-trifluoromethylthiopyrazole (8.4 g) in chloroform (60 ml) containing diphenyl disulphide (8.72 g) was treated with t-butyl nitrite (4.12 g) over a period of 5 minutes at room temperature. The solution was heated at 50° C. for 2 hours, cooled to room temperature, and washed with water (2×50 ml). After drying over anhydrous magnesium sulphate, the solution was evaporated in vacuo to give an orange liquid. This was purified by chromatography, eluting with dichloromethane/hexane 1:3), followed by recrystallisation from hexane to give 3-cyano-1-2,6-dichloro-4-trifluoromethylphenyl)-5-phenylthio-4-trifluoromethylthiopyrazole 1.8 g) as a white solid, m.p. 84°–86° C.

EXAMPLE 2

A solution of 5-bromo-3-cyano-1-(2,6-dichloro-4-trifluoromethylphenyl)-4-trifluoromethylsulphonylpyrazole (3.0 g) in dry tetrahydrofuran (32 ml, stirred under nitrogen at −78° C., was treated with a solution of n-butyllithium in hexane (2.8 ml of a 2.5M solution) over a period of 5 minutes. After 1 hour at −78° C., a solution of benzyl thiocyanate (0.95 g) in tetrahydrofuran (2 ml) was added. The stirred mixture was allowed to warm slowly to room temperature during 16 hours, then poured onto ice/water 50 ml) and extracted with ether (3×50 ml). The combined extracts were dried over anhydrous magnesium sulphate, evaporated in vacuo, and purified by chromatography, eluting with ethyl acetate/hexane (2:98). The product was triturated with hexane to give 5-benzylthio-3-cyano-1-(2,6-dichloro-4-trifluoromethylphenyl)-4-trifluoromethylsulphonylpyrazole (0.25 g), as a white solid, m.p. 117°–119° C.

We claim:

1. An N-phenylpyrazole derivative of the formula:

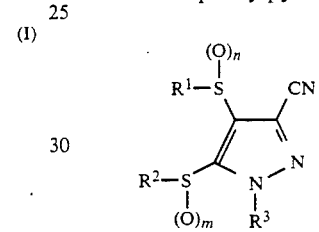

wherein $R^1$ represents a straight or branched chain alkyl group containing up to 4 carbon atoms which may be unsubstituted or substituted by one or more halogen atoms; $R^2$ represents a phenyl or benzyl group optionally substituted on the aromatic ring by one or more halogen atoms; optionally halogenated alkyl, alkoxy, alkylthio, alkylsulphinyl or alkysulphonyl groups containing up to 4 carbon atoms and being straight or branched chain; or nitro, cyano or acyl groups; and when $R^2$ represents benzyl, optionally α-substituted by a straight or branched alkyl group containing up to 4 carbon atoms; $R^3$ represents a phenyl group substituted in the 2-position by a halogen atom; in the 4-position by a straight or branched chain alkyl or alkoxy group containing from 1 to 4 carbon atoms which may be unsubstituted or substituted by one or more halogen atoms; and optionally in the 6-position by a halogen atom; and m and n are independently 0, 1 or 2.

2. A compound according to claim 1 wherein $R^1$ represents a trihalomethyl group.

3. A compound according to claim 2 wherein $R^1$ represents a trifluoromethyl group.

4. A compound according to any one of claims 1, 2 and 3 wherein the 4- position in the phenyl group represented by $R^3$ is substituted by trifluoromethyl or trifluoromethoxy.

5. A compound according to any one of claims 1, 2, and 3 wherein $R^3$ represents a phenyl group which is 2,6-dichloro-4-difluoromethoxy, 2-chloro-4-trifluoromethyl, 2-bromo-6-chloro-4-trifluoromethyl, 2,6-dibromo-4-trifluoromethyl or 2-bromo-4-trifluoromethyl substituted.

6. A compound according to any one of claims 1, 2 and 3 wherein the phenyl group represented by $R^3$ is 2,6-dichloro-4-trifluoromethyl or 2,6-dichloro-4-trifluoromethoxy substituted.

7. A compound according to claim 1 which is 3-cyano-1-(2,6-dichloro-4-trifluoromethylphenyl)-5-phenylthio-4-trifluoromethylthiopyrazole or 5-benzylthio-3-cyano-1-(2,6-dichloro-4-trifluoromethylphenyl)-4-trifluoromethylsulphonylpyrazole.

* * * * *